US008262681B1

(12) United States Patent
Gerrah et al.

(10) Patent No.: US 8,262,681 B1
(45) Date of Patent: Sep. 11, 2012

(54) DEVICE AND METHOD FOR PERFORMING ENDOLUMINAL PROXIMAL ANASTOMOSIS

(76) Inventors: Rabin Gerrah, New York, NY (US); Omid David Tabibi, Bay-Yam (IL)

( * ) Notice: Subject to any disclaimer, the term of this patent is extended or adjusted under 35 U.S.C. 154(b) by 839 days.

(21) Appl. No.: 12/292,703

(22) Filed: Nov. 24, 2008

Related U.S. Application Data

(60) Provisional application No. 61/004,035, filed on Nov. 23, 2007.

(51) Int. Cl.
*A61B 17/04* (2006.01)
*A61F 2/06* (2006.01)
(52) U.S. Cl. ............................ 606/153; 623/1.23
(58) Field of Classification Search ........... 606/153, 606/155, 151, 139, 157, 158, 219, 184, 185, 606/143, 213, 142, 170, 144, 148; 623/1.11, 623/1.36, 1.23, 1.13
See application file for complete search history.

(56) References Cited

U.S. PATENT DOCUMENTS

| 5,234,407 | A |   | 8/1993  | Teirstein |         |
|-----------|---|---|---------|-----------|---------|
| 5,676,670 | A |   | 10/1997 | Kim       |         |
| 5,695,504 | A |   | 12/1997 | Gifford, III |      |
| 5,875,782 | A | * | 3/1999  | Ferrari et al. | 128/898 |
| 6,068,637 | A |   | 5/2000  | Popov     |         |
| 6,565,582 | B2 |  | 5/2003  | Gifford   |         |
| 6,869,437 | B1 |  | 3/2005  | Hausen    |         |
| 7,022,131 | B1 |  | 4/2006  | Derowe    |         |
| 7,115,136 | B2 |  | 10/2006 | Park      |         |
| 2001/0047180 | A1 | * | 11/2001 | Grudem et al. | 606/153 |
| 2002/0077637 | A1 | * | 6/2002 | Vargas et al. | 606/153 |
| 2002/0099394 | A1 | * | 7/2002 | Houser et al. | 606/153 |
| 2004/0034377 | A1 | * | 2/2004 | Sharkawy et al. | 606/153 |
| 2004/0138685 | A1 | * | 7/2004 | Clague et al. | 606/167 |
| 2004/0158267 | A1 | * | 8/2004 | Sancoff et al. | 606/153 |
| 2007/0235044 | A1 |   | 10/2007 | Benetti |         |
| 2008/0161839 | A1 |   | 7/2008 | Shalev |         |
| 2008/0255506 | A1 |   | 10/2008 | Wilson |         |

FOREIGN PATENT DOCUMENTS

WO  WO00/18303  4/2000

OTHER PUBLICATIONS

Jörg Kempfert, et al; "Twelve-Month Patency With the PAS-Port Proximal Connector Device: A Single Center Prospective Randomized Trial". The Society of Thoracic Surgeons, Ann Thorac Surg 2008;85:1579-85.

L. Wiklund, et al; "A new mechanical connector for distal coronary artery anastomoses in coronary artery bypass grafting: A randomized, controlled study".The Journal of Thoracic and Cardiovascular Surgery • Jan. 2005. p. 146-150.

J.F. Gummert, et al; "Anastomotic devices for coronary artery bypass grafting: Technological options and potential pitfalls". Computers in Biology and Medicine 37 (2007) 1384-1393.

(Continued)

*Primary Examiner* — Kathleen Sonnett
*Assistant Examiner* — Jocelin Tanner
(74) *Attorney, Agent, or Firm* — Graeser Associates International Inc; Dvorah Graeser

(57) ABSTRACT

The present invention is of a method for performing an anastomosis and in particular, to such a method in which an end-to-side vessel endoluminal proximal anastomosis is performed in a minimally invasive CABG procedure.

9 Claims, 7 Drawing Sheets

OTHER PUBLICATIONS

Yaron Bar-El, et al; "CorLink™ Sutureless Aortic Anastomotic Device: Results of an Animal Study". Journal of Surgical Research 115, 127-132 (2003) doi:10.1016/S0022-4804(03)00191-4.

Edward G. Shifrin, et al; "Developments in instrumentation: II. Mechanical vascular anastomoses". Chapter 8. p. 63-69. (Sep. 19, 2006).

B. D. Hoagland, et al; "Devices to Improve Coronary Artery Bypass Grafting (CABG) Surgery". Proceedings of the 26th Annual International Conference of the IEEE EMBS San Francisco, CA, USA • Sep. 1-5, 2004. p. 3792-3795.

Sary F. Aranki, et al; "Evaluation of the Enclose Proximal Anastomosis Device in Coronary Artery Bypass Grafting". The Society of Thoracic Surgeons Ann Thorac Surg 2005;80:1091-5.

Piergiorgio Tozzi, et al; "Sutureless coronary anastomoses: revival of old concepts". European Journal of Cardiothoracic Surgery 22 (2002) 565-570.

Marc P. Buijsrogge, et al; "Sutureless coronary anastomosis with an anastomotic device and tissue adhesive in off-pump porcine coronary bypass grafting". The Journal of Thoracic and Cardiovascular Surgery • Apr. 2002 p. 788-794.

* cited by examiner

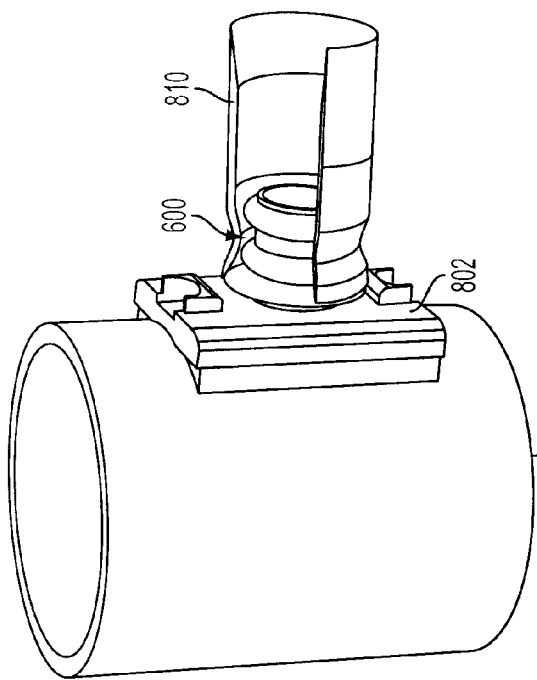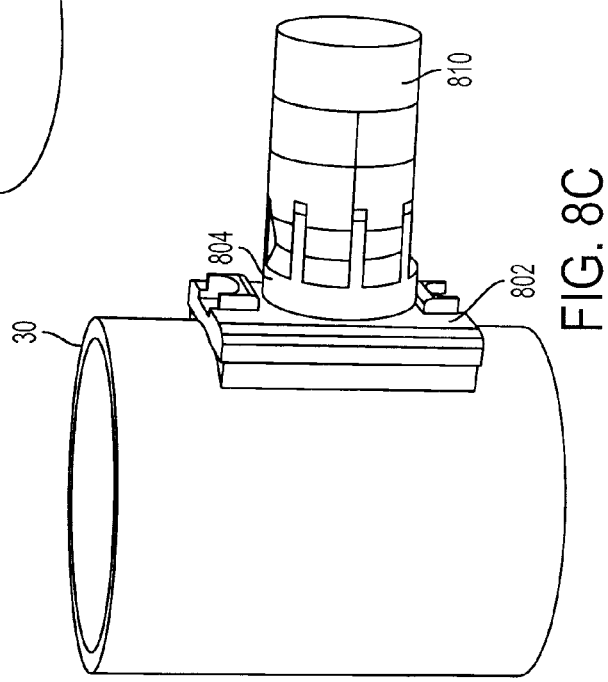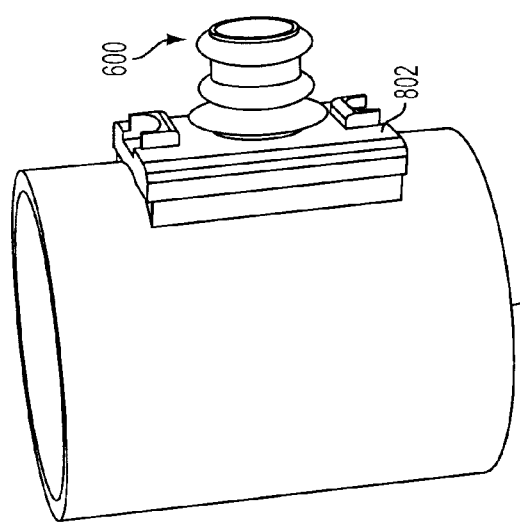

DEVICE AND METHOD FOR PERFORMING ENDOLUMINAL PROXIMAL ANASTOMOSIS

This Application claims priority from U.S. Provisional Application No. 61/004,035, filed on Nov. 23, 2007 which is hereby incorporated by reference as if fully set forth herein.

FIELD OF THE INVENTION

The present invention relates to a method for performing an anastomosis and in particular, to such a method in which an end-to-side vessel anastomosis is performed in a Coronary Artery Bypass Graft (CABG) procedure.

BACKGROUND OF THE INVENTION

Heart disease is defined as any disorder that affects the heart's ability to function properly, and its most common cause is narrowing or blockage of the coronary arteries, which supply blood to the heart itself. The treatment for coronary artery disease is mainly by angioplasty and surgical revascularization, known as Coronary Artery Bypass Graft (CABG). Due to the nature of the disease, CABG has become one of the most commonly performed procedures in the world. Coronary artery bypass graft surgery (CABG) is a surgical procedure to restore blood flow to ischemic heart muscle whose blood supply has been compromised by occlusion or stenosis of one or more of the coronary arteries.

Coronary artery disease is mostly caused by localized blocks, with resultant disruption of blood flow and deprivation of heart muscle from energy and oxygen. In order to bypass a blockage in a coronary artery, native blood vessels harvested from other parts of the body—or rarely synthetic vessels—are connected to the blocked vessels beyond the lockage. The bypassing vessels are in communication with a source of arterial blood, mostly from aorta, and in other cases the internal mammary arteries. By doing so, the blood supply is resumed again to the continuity of the vessel beyond the blockage, and therefore to target heart muscle. The number of connections on heart usually corresponds to the number of significant blockages.

An important phase during CABG is the performance of the bypass itself where two blood vessels are joined in a process termed anastomosis. Anastomosis is the surgical joining of biological tissues, especially the joining of tubular organs to create intercommunication between them. Vascular surgery often involves creating an anastomosis between blood vessels or between a blood vessel and a vascular graft to create or restore a blood flow path to essential tissues. As in other anastomoses, the surgeon must securely and accurately suture the proximal end of each conduit to the patient's aorta in order to obtain a non-disturbed blood flow.

The procedure of bypass surgery is performed in majority of conventional cases through the midline incision and sternotomy to open the chest. During the past few years, however, there has been a movement away from open-chest surgery toward minimally invasive cardiac surgery. Minimally invasive cardiac surgery poses significant challenges for the surgeon. The CABG procedures presently being performed in a minimally invasive manner are typically carried out through incisions made between the ribs, which require the surgeon to operate with considerably less access to the heart and aorta as compared to open-chest. During minimally invasive procedures the anastomosis is performed by suturing the vessels and/or anastomosis connectors through the small incisions, usually using direct vision through regular magnifier loupes, by endoscopic instruments, or using video assisted vision.

At present, many vascular anastomoses continue to be performed by conventional hand suturing, with an open chest. The move to minimally invasive CABG, intended to reduce the morbidity of open heart CABG surgery procedures, has made evident the need for improved tools, devices and methods for performing anastomoses.

SUMMARY OF THE INVENTION

The background art does not teach or suggest a device or method for performing minimally invasive anastomoses which is efficient, easier to perform than current such procedures and yet which provides a strong and secure graft.

The present invention overcomes these deficiencies of the background by providing a method for performing anastomoses in a minimally invasive manner and in particular an end-to-side anastomosis between blood vessels, conduits or other hollow organs and vessels. It is also desirable to provide an anastomosis device which minimizes the trauma to the blood vessels while performing the anastomosis, therein minimizing the overall time used for the procedure.

Within the context of this application the term femoral port or femoral artery port refers to an access port made in the groin area to gain access to the femoral artery.

Within the context of this application the term thoracic port refers to an access port made via a small incision made in the intercostal spaces of the chest, between the ribs to gain access to the chest cavity.

Within the context of this application the term preoperative measures refers to any preparative steps leading up to the procedure itself including planning stages up to the initial incision, using tools, devices and/or methods as is known and accepted in the art; such measures may optionally include but are not limited to defining the graft site using imagery tools, using a chest CT to identify the incision site and the like.

Although the forthcoming description of a device and method relates to a minimally invasive keyhole CABG proximal anastomosis procedure the foregoing it will be appreciated that a skilled artisan could apply the device and method of the present invention to other anastomisis procedures and in particular to a conventional open heart CABG proximal anastomosis procedure.

A preferred embodiment of the present invention provides for an improved method for facilitating vascular end-to-side anastomosis by providing a method for increased maneuverability when performing vascular anastomosis most preferably proximal anastomosis in a minimally invasive CABG procedure for example through at least one keyhole or port access. Most preferably a surgeon is provided with increased maneuverability by approaching the anastomosis site from at least two locations across the anastomosis site or graft site. Most preferably an endoluminal side of the graft site is provided from an internal surface, within the lumen of the graft site, while an external surface of the graft site is provided from an external surface, outside the lumen of the graft site.

Most preferably both of the endoluminal and external surface of the graft site are accessed via a minimally invasive port. Preferably, the endoluminal side of the graft site may be accessed through a femoral artery port while the external surface of the graft site accessed through a thoracic port. Optionally, the endoluminal side of the graft site may be accessed through a thoracic port while the external surface of the graft site accessed through a femoral port. For example a proximal aortic anastomosis may be performed according to the present invention wherein an endoluminal side of the graft site is provided from within the lumen of the aorta approached from a femoral port while the external surface of the graft site is provided on the surface of the aorta, through a thoracic port, therein providing for an endoluminal anastomosis.

An optional embodiment of the present invention provides for a femoral port that is used to access the endoluminal side of the graft site using a set of femoral port access devices comprising at least one or more of: a clip introducer for introducing devices through the femoral port to the endoluminal side of the graft site and optionally to perforate the anastomosis graft site; a guidewire for guiding a plurality of devices through the vasculature; an endoluminal introducer preferably providing tools for perforating the anastomosis graft site from the endoluminal side of the graft site, optionally and preferably including carrying the connection device or connector itself, a guidewire grabber for accepting and/or manipulating other devices, objects or tissue, preferably and optionally originating from the external surface of the graft site; and an anastomosis clip according to the present invention disposed on the introducing needle.

An optional embodiment of the present invention provides for a thoracic port that is used to access the external surface of the anastomosis graft site using a set of thoracic port access devices comprising at least one or more of: a thoracic small retractor, a thoracoscopic arm optionally and preferably having a vacuum-operated isolating ring stabilizer, for stabilizing the anastomosis graft site; ring shaped gripper handles for manipulating an anastomosis clip; or an anastomosis clip holder ring for fastening an anastomosis clip with a grafted vessel; and the like.

A further embodiment of the present invention provides for an anastomosis clip preferably comprising at least two or more sections: a first section providing a base, optionally referred to as an intraluminal base for anchoring the anastomosis clip to the intraluminal side of the graft site; a second section protruding from the anastomosis clip base forming a tube for accepting a grafted vessel at the external surface of the graft site. Optionally the first section provides a wide base for anchoring the grafted vessel onto the accepting conduit. Preferably the first section comprises a diameter larger than that of the second section and the graft site. Most preferably, the first and second sections form a continuous single piece anastomosis connector.

Optionally and preferably, the anastomosis clip according to the present invention may be provided with a third section disposed along the length of the protruding portion of the clip, most preferably at its base. Preferably the third section provides for receiving an external supportive and/or anchoring member to stabilize the wide base of the clip across the graft site. Preferably the external supportive structure provides structural support for preventing the clip from moving from the graft site and into the intraluminal space, while the wide base of the anastomosis clip provides for support preventing the clip from moving away from the graft site.

Optionally and preferably, the second section protruding from the anastomosis clip base forms a tube like structure for accepting a graft at the external surface of the graft site comprises hooks, clasp, or other the like processes for holding, grasping, or coupling the graft to the clip and in particular to the second section of the clip following placement.

Optionally the anastomosis clip according to the present invention may be used to form a plurality of graft angles as determined by medical personnel, the parameters or configuration of the anastomosis site, graft site anatomy or physiology, or a combination thereof. Most preferably the angle is defined by the angle formed between the clip's first section and its second section. Optionally, the angle formed may be up to about 90 degrees, most preferably about 30 degrees or about 45 degrees or about 60 degrees and optionally 90 degrees.

Optionally the anastomosis clip according to the present invention may be used to form a plurality of graft angles most preferably determine by the angle formed between the clip's third section and its second section. Optionally, the angle formed may be up to about 90 degrees, most preferably about 30 degrees or about 45 degrees or about 60 degrees and optionally 90 degrees.

The anastomosis clip according to the present invention is optionally made of a mesh, stent, solid, or continuous structure. Most preferably the anastomosis clip is formed of biocompatible and medical grade material for example including but not limited to nitinol, medical grade plastic, metals, alloys, hybrids or the like biocompatible material as is known and accepted in the art.

Optionally, the anastomosis connector clip according to the present invention may optionally and preferably be made of a dilatable and/or otherwise self-expanding structure that is optionally shaped according to the graft site or vasculature at the graft site angle or the like.

The anastomosis connector clip according to the present invention is preferably expandable from a low-profile compressed condition to a larger profile expanded condition, wherein the resilient material urges the vessel supporting structure to expand radially, and to thereby apply radial force against the blood vessel's inner wall surface. For example, balloon angioplasty may be utilized to provide the final shape of the connector clip.

A preferred embodiment of the present invention comprises an anastomosis connector clip that may optionally be composed of a shape memory alloy (SMA) including but not limited to nickel titanium alloy (NiTi), also known as nitinol, having a transition temperature around body temperature. They may also (additionally or alternatively) optionally comprise a shape memory polymer (SMP) that can be triggered in response to changes in heat, pH, electric or magnetic fields. For example, the anastomosis connector clip of the preferred embodiment of the present invention may optionally be introduced into a blood vessel in its collapsed formation having a small profile. Once in place and after it is released from the constraining catheter, the device preferably expands to the appropriate diameter and into its final or "memorized" shape.

The anastomosis clip according to the present invention, may optionally be coupled with a medicament for example such as a drug eluting stent as is known in the art, for example and without limitation, including one or more of blood thinners, wound healing drugs, heparin, Sirolimus, Paxitaxel, Tacrolimus or the like.

A preferred embodiment of the present invention provides for a method for performing an endoluminal proximal anastomosis using a femoral port and a thoracic port preferably comprises the following stages. First, a thoracic port is defined by performing a thoracotomy to allow a thoracic port, most preferably making an incision of up to about 5 cm, preferably about 4-5 cm and optionally about 2 to 3 cm. Most preferably the thoracotomy is performed on one side of the body, preferably where the bypass graft is to be anastomosized. Optionally, a thoracotomy is performed on one or both sides of the body. Optionally guided imagery is provided by endoscopy or the like imagery tools as is known and accepted in the art during any one or more of the below stages, although this is not necessary.

Next, the anastomosis graft site on the external surface of the aorta is identified.

The graft site is stabilized and isolated by introducing an isolating ring stabilizer most preferably equipped with a vacuum tube to introduce suction to stabilize the aorta during the procedure. Most preferably the thoracic port is used to introduce the isolating ring stabilizer to the external surface of the graft site. Preferably, the isolating ring stabilizer is disposed over the external surface of the graft site, thereby exposing and stabilizing the graft site. Optionally and preferably vacuum will be applied around the graft site, most preferably by securing an optional flexible pillow preferably associated with isolating ring stabilizer that is attached to the vacuum tube over the graft site, thereby providing the graft site with support and stability. The flexible vacuum pillow is introduced through the thoracic port using a thoracic retractor The isolating ring stabilizer may optionally be configured to have various geometric shapes and or sizes in accordance with the graft site geometry. Most preferably, the isolating ring stabilizer shape may be chosen from the shapes comprising ellipsoid, elliptic, circular or the like. The isolating ring stabilizer is preferably provided from material known and accepted in the art; most preferably it is composed of flexible material so as to allow it to align itself with the shape and contour of the graft site for example on the aorta. Optionally, the isolating ring may be made of rigid materials.

The exposed and stabilized graft site is punctured with a needle or other sharp instrument, providing a graft site port through which a guidewire is threaded. Most preferably, the guidewire is advanced through the vasculature from the graft site, most preferably at the ascending aorta through to the femoral artery, to the site where the femoral artery port is to be defined.

The femoral port is then defined as is known and accepted in the art, for example by making an incision in the groin region to access the femoral artery.

The guidewire is then exposed through an extrusion from the femoral port. Most preferably the guidewire, now descending from the graft site through to the femoral port, is located and exposed by manipulating a needle and/or wire grabber for example a loop shaped grabber.

The exposed guidewire is threaded with a loaded clip introducer preferably comprising a tissue perforating head and an anastomosis connector, for example including but not limited to the anastomosis clip according to an optional embodiment of the present invention.

The loaded clip introducer is optionally introduced through the femoral port, and is then moved through vasculature, to the anastomosis graft site, reaching the endoluminal side of the graft site.

Optionally and preferably, if the clip introducer is already equipped with a tissue perforating head, the tissue perforating head perforates the graft site endoluminally, preferably traversing and defining the graft site therein creating the graft site channel. Alternatively, a separate tool from the clip introducer could be used to make a larger hole, such as a punch for example.

Most preferably, after the graft site channel has been made, the clip introducer deploys the anastomosis connector or clip according to an optional embodiment of the present invention. Also most preferably, the anastomosis connector is placed such that its wide base remains endoluminally, or intraluminally within the grafted vessel such as the aorta while the protruding section traverses the graft site channel. Optionally, deployment of the anastomosis connector may be implemented via a self expanding technology as is known and accepted in the art, for example by expanding an angioplasty catheter balloon.

Most preferably the anastomosis connector is held in place, traversing the graft site opening, by interacting with a gripper introduced through the thoracic port. Optionally, the gripper is associated with the isolating ring stabilizer over the graft site.

Preferably and optionally, an external support member is introduced through the thoracic port and disposed on top of the anastomosis clip over to the graft site, thereby providing additional support and or stability to the graft site, and also preferably anchoring the anastomosis ring onto the graft site. Stabilization is performed through the conduit itself and its fastening device, without requiring the additional ring.

The graft is then introduced through the thoracic port and disposed over the protruding section of the anastomosis clip.

Optionally, the process may feature introducing an anastomosis clip fastening device, for example including but not limited to a ring, over the connector clip to securely fasten the graft to the anastomosis connector clip body. The fastening device may optionally be used to secure the anastomosis clip to provide structural support for preventing the clip from moving from the graft site and into the intraluminal space, thereby making the third section of the anastomosis clip redundant (and optionally eliminated from the device).

The fastening device may optionally and preferably form and determine the required graft angle. Optionally, the fastening device may form up to about 90 degrees, most preferably about 30 degrees or about 45 degrees or about 60 degrees, and optionally exactly 90 degrees. However, the angle of the fastening device is preferably determined according to the angle provided by the clip itself. Optionally the connector clip ring fastens the connector clip and graft together by applying pressure, for example, fastening may optionally be achieved by methods including but not limited to applying pressure, stapling, releasing or inflating an angioplasty balloon or the like coupling tools. Optionally, fastening may be achieved by use of hooks along an external ring clip.

Tools, devices for example including clip introducer, vacuum stabilizer, guidewire and the like, are then evacuated from the body cavity.

An optional, additional and different embodiment of the present invention provides for a method for performing an endoluminal anastomosis comprising using a femoral port to access the endoluminal side of the graft site and a thoracic port to access the external surface of the graft site. For this different embodiment, the method features the stage of defining a femoral port and a thoracic port. Each such port may optionally be formed as previously described. Preferably the thoracotomy is performed on the side of the body where the bypass graft is to be anastomosized. Next, a guidewire system is introduced and threaded, as is known and accepted in the art, through the vasculature from the femoral port toward the thoracic port. Optionally and preferably the guidewire is threaded through the graft site and preferably coupled or otherwise associated with the thoracic port, therein providing a guidewire connection between the femoral and thoracic ports.

Next, a loaded clip introducer preferably comprising a tissue perforating head and an anastomosis connector, for example including but not limited to the anastomosis clip according to an optional embodiment of the present invention, is navigated along the guidewire through the femoral artery ascending to the ascending aorta to the anastomosis graft site, reaching the endoluminal side of the graft site.

The appropriate anastomosis graft site is identified, optionally through some type of guided imaging, which may optionally be provided by fluoroscopy, CT (computerized tomography), endoscopy, ultrasound and so forth.

Once the graft site is determined, an isolating ring stabilizer is introduced through the thoracic port to the external surface of the graft site. Preferably, the isolating ring stabilizer is disposed over the external surface of the graft site. Preferably and optionally vacuum will be applied over the graft site, most preferably securing the isolating ring stabilizer over the graft site, thereby providing support in the circumferential area around the anastomosis.

Optionally and preferably, if the clip introducer is already equipped with a tissue perforating head, the tissue perforating head perforates the graft site endoluminally, preferably traversing and defining the graft site therein creating the graft site channel. Alternatively, a separate tool from the clip introducer could be used to make a larger hole, such as a punch for example.

Most preferably, after the graft site channel has been made, the clip introducer deploys the anastomosis connector or clip according to an optional embodiment of the present invention. Also most preferably, the anastomosis connector is placed such that its base remains endoluminally while the protruding section traverses the graft site channel. Optionally, deployment of the anastomosis connector may be implemented via a self expanding technology as is known and accepted in the art, for example by expanding an angioplasty catheter balloon.

The anastomosis connector clip is passed through to the graft site by the guidewire. Most preferably the anastomosis connector is held in place, traversing the graft site opening, by interacting with a gripper introduced through the thoracic port. Optionally, the gripper is associated with the isolating ring stabilizer over the graft site.

Optionally, an external support member is introduced through the thoracic port and disposed on top of the anastomosis clip over the graft site, thereby providing additional support and or stability to the graft site, and also preferably anchoring the anastomosis ring onto the graft site. Stabilization is performed through the conduit itself and its fastening device, without requiring the additional ring.

The graft is then introduced through the thoracic port and disposed over the protruding section of the anastomosis clip.

Optionally, the process may feature introducing an anastomosis clip fastening device, for example including but not limited to a ring, over the connector clip to securely fasten the graft to the anastomosis connector clip body. The fastening device may optionally and preferably form and determine the required graft angle. Optionally, the fastening device may form up to about 90 degrees, most preferably about 30 degrees or about 45 degrees or about 60 degrees, and optionally exactly 90 degrees. However, the angle of the fastening device is preferably determined according to the angle provided by the clip itself. Optionally the connector clip ring fastens the connector clip and graft together by applying pressure, for example, fastening may optionally be achieved by methods including but not limited to applying pressure, stapling, releasing or inflating an angioplasty balloon or the like coupling tools. Optionally, fastening may be achieved by use of hooks along an external ring clip.

Tools, devices for example including clip introducer, vacuum stabilizer, guidewire and the like, are then evacuated from the body cavity.

According to some embodiments of the present invention, there is provided a method for performing a minimally invasive endoluminal proximal CABG anastomosis using an anastomosis connector clip comprising: performing a thoracotomy on at least one side of the body to define a thoracic port; defining a femoral artery port; stabilizing the graft site with an isolating ring stabilizer disposed over the external surface of the graft site to provide a stabilized graft site; puncturing the stabilized graft site to provide a graft site port through which a guidewire is threaded; advancing the guidewire through the vasculature to the femoral artery port; deploying the anastomosis connector clip from the endoluminal side through to the external surface of the graft site channel through the guidewire; perforating the graft site forming a graft site channel; supporting the anastomosis connector clip in the graft site channel from the external surface of the graft site; coupling a connector clip external support member to the anastomosis connector clip over the graft site channel; disposing a graft over the anastomosis connector clip on the graft site external surface; and coupling the graft and the connector clip external support member to the connector clip.

Preferably, the method further comprises deploying an anastomosis clip fastening device for securely fastening the graft to the anastomosis connector clip. Optionally, the thoracotomy is performed on both sides of the body. Also optionally, the graft site isolation and stabilization is achieved using vacuum. Preferably, the vacuum is applied to a flexible pillow associated with the isolating ring stabilizer disposed over the graft site.

Optionally the anastomosis connector clip is introduced from the femoral port over the guidewire using a clip introducer loaded with the anastomosis connector clip. Preferably, the graft site channel is perforated with a tool originating from the femoral port over the guidewire. More preferably, the tool is separate from the clip introducer. Alternatively and more preferably, the tool is combined with the clip introducer. Most preferably, the tool is selected from the group consisting of a needle introducer and a tissue punch.

Unless otherwise defined, all technical and scientific terms used herein have the same meaning as commonly understood by one of ordinary skill in the art to which this invention belongs. The materials, methods, and examples provided herein are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 8A-C depicts an exemplary anastomosis connector clip within the graft site according to an optional embodiment.

DESCRIPTION OF THE PREFERRED EMBODIMENTS

The present invention is of a method for performing an anastomosis and in particular, to such a method in which an end-to-side vessel endoluminal proximal anastomosis is performed in a minimally invasive CABG procedure.

The principles and operation of the present invention may be better understood with reference to the drawings and the accompanying description.

Figure 1:
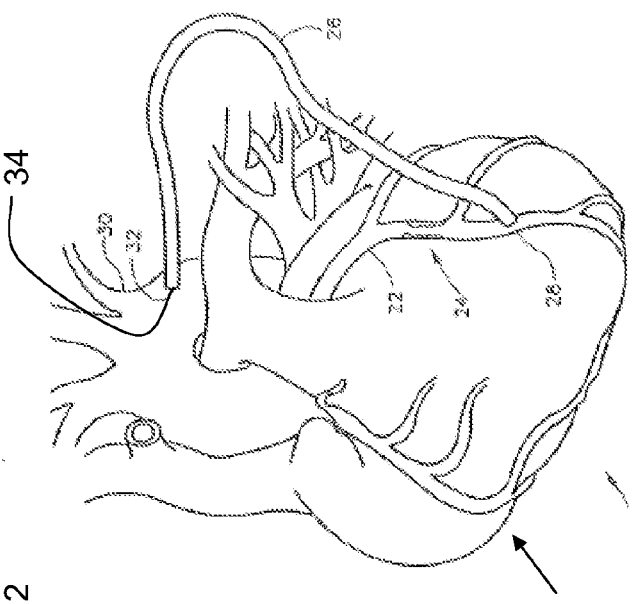
FIG. 1 shows a heart having a coronary bypass.

FIG. 1 shows a heart 100 with a bypass graft 26 wherein the proximal anastomosis graft site 32 is located on the aorta 30 such that the graft site has an external surface 34 as well as an endoluminal surface (not shown) from within the aorta.

Figure 2:
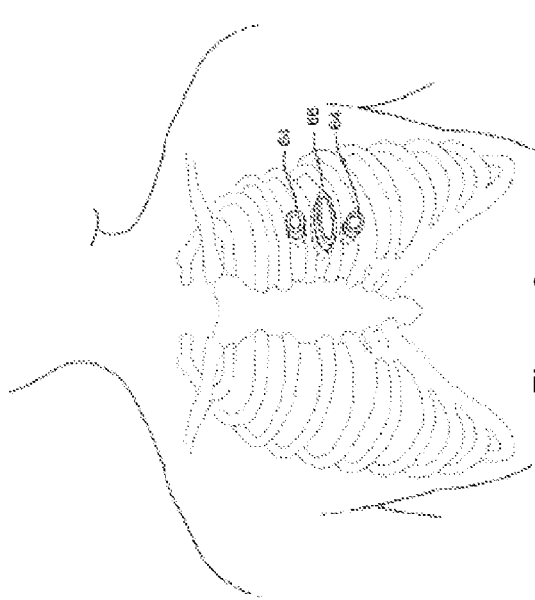
FIG. 2 shows a schematic diagram of an exemplary minimally invasive thoracic ports preferably used as an access point for the external surface of the graft site according to the present invention.

FIG. 2 shows exemplary minimally invasive thoracic ports 64 and 66 having variable sizes for performing an endoluminal proximal anastomosis. Most preferably the thoracic ports 64 and or 66 are used to access the external surfaces of the graft site.

Figure 3:
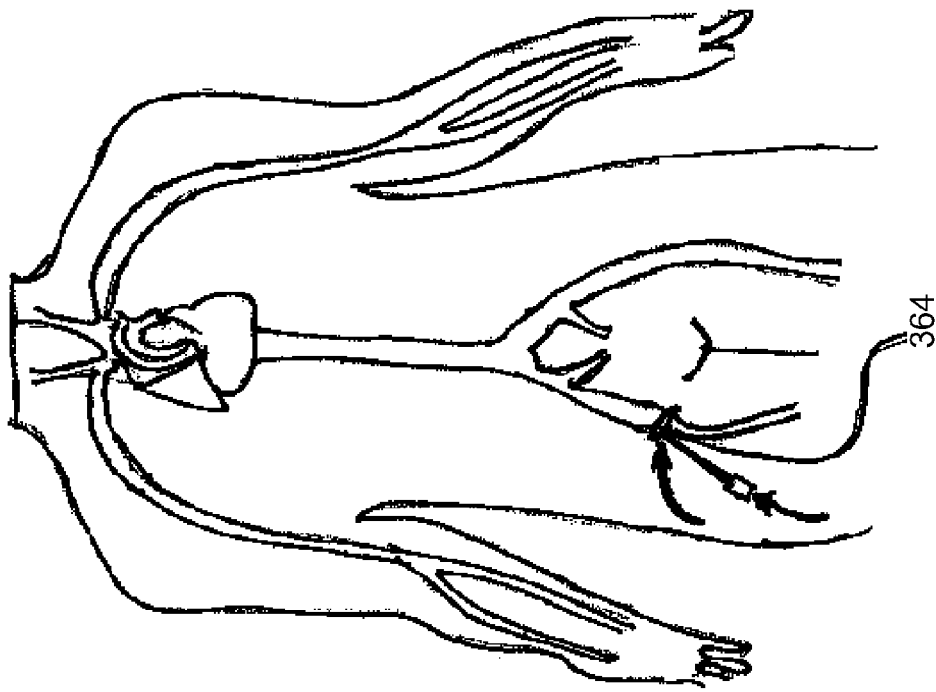
FIG. 3 shows a schematic diagram of an exemplary minimally invasive femoral access port preferably used to access the endoluminal side of the graft site according to the present invention.

FIG. 3 shows an exemplary minimally invasive femoral port 364 for performing an endoluminal proximal anastomosis. Most preferably femoral port 364 is used to access the endoluminal surfaces of the graft site.

Figure 4:
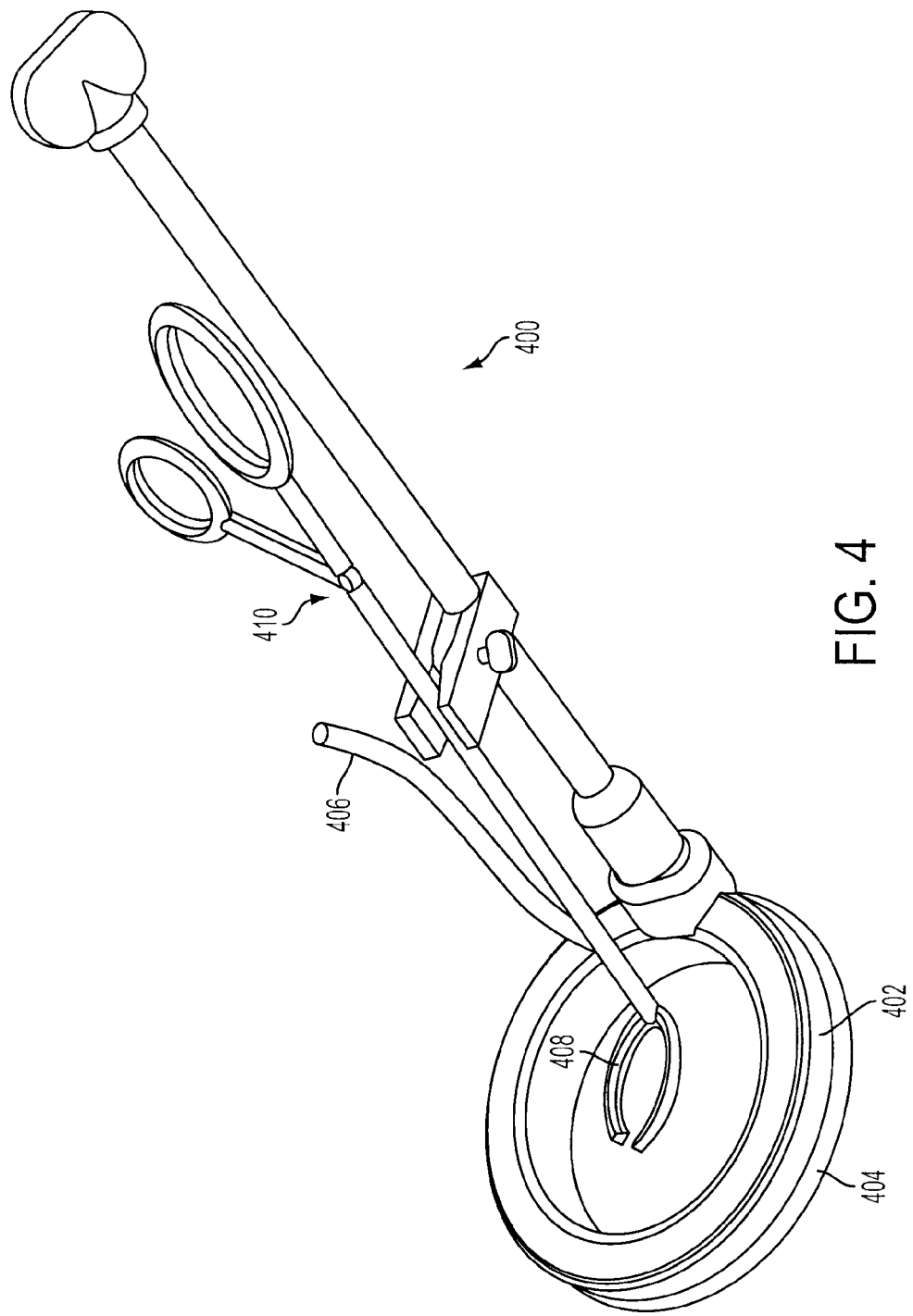
FIG. 4 depicts an exemplary thoracic anastomosis device used to perform the anastomosis according to the present invention.

FIG. 4 provides a schematic depiction of an exemplary thoracoscopic arm 400 used to manipulate the external surface of a graft site 32 of FIG. 1 through a thoracic port 64 of FIG. 2. Optionally thoracoscopic arm 400 optionally and preferably comprises a vacuum-operated isolating ring stabilizer 402 optionally associated with a flexible contact pillow 404. Preferably a vacuum tube 406 is used to provide vacuum and/or suction to the external surface of the graft site therein preferably stabilizing the anastomosis graft site from the eternal side. Preferably an anastomosis clip fastening device 408 is controllably associated with thoracoscopic arm 400 optionally via holder 410 allowing a user to manipulate an anastomosis clip or connector (not shown), graft (not shown) from the external surface of the graft site.

The anastomosis clip fastening device 408 may optionally be provided in a variety of shapes or forms so as to allow it to securely associate and controllably manipulate an anastomosis clip connector. Optionally, gripper 408 may take the shapes for example including but not limited to a ring, ellipsoid, elliptic, circular or the like geometric shape.

Figure 5:
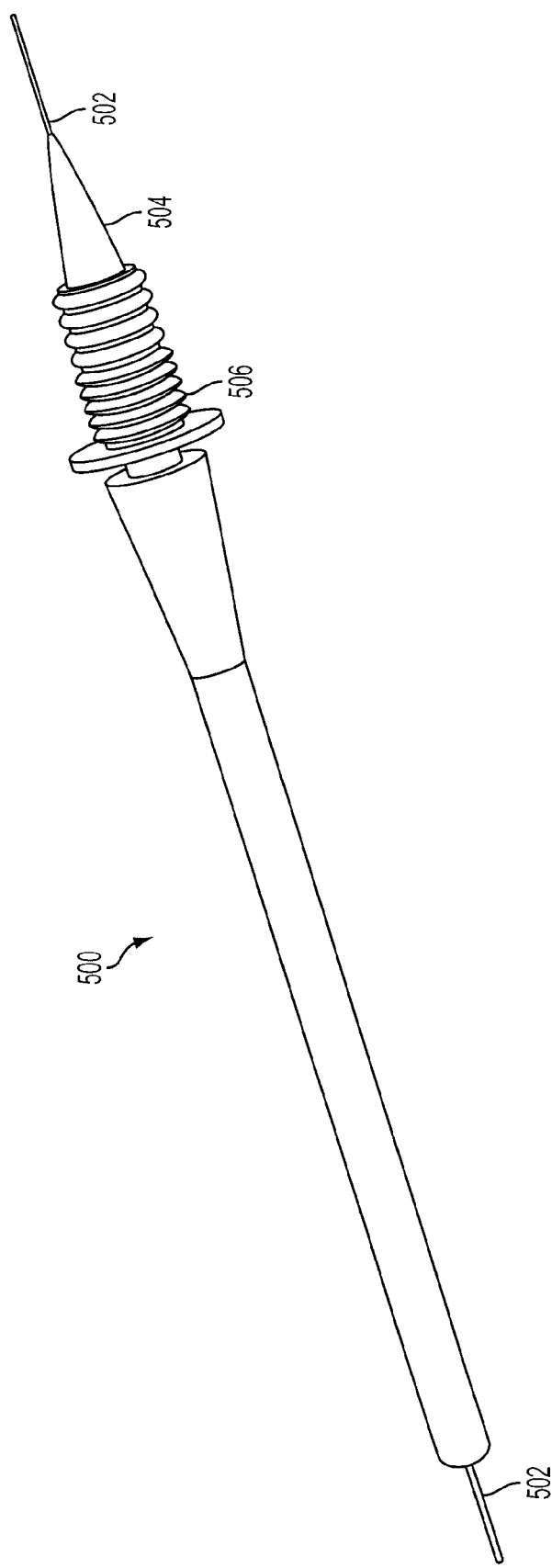
FIG. 5 depicts an exemplary femoral anasotmosis devices utilized in performing an anastomosis according to the present invention.

FIG. 5 depict an exemplary clip introducer 500 preferably used through the femoral port 364 of FIG. 3 in accordance with an optional embodiment of the present invention. FIG. 5A depicts an optional and preferable clip introducer 500 threaded over guidewire 502. Clip introducer 500 is preferably loaded comprising a tissue perforating head 504 and an anastomosis connector clip 506. Loaded clip introducer 500 is optionally introduced through the femoral port, and is then moved through vasculature along guidewire 502 to the anastomosis graft site, reaching the endoluminal side of the graft site. Optionally perforating head 504 is used to perforate the graft site endoluminally preferably traversing and defining the graft site therein creating the graft site channel. Once the graft site channel is defined then anastomosis connector clip 506 may be deployed from introducer 500 into the graft site preferably controllably associated with anastomosis clip fastening device 408 of FIG. 4.

Figure 6A:
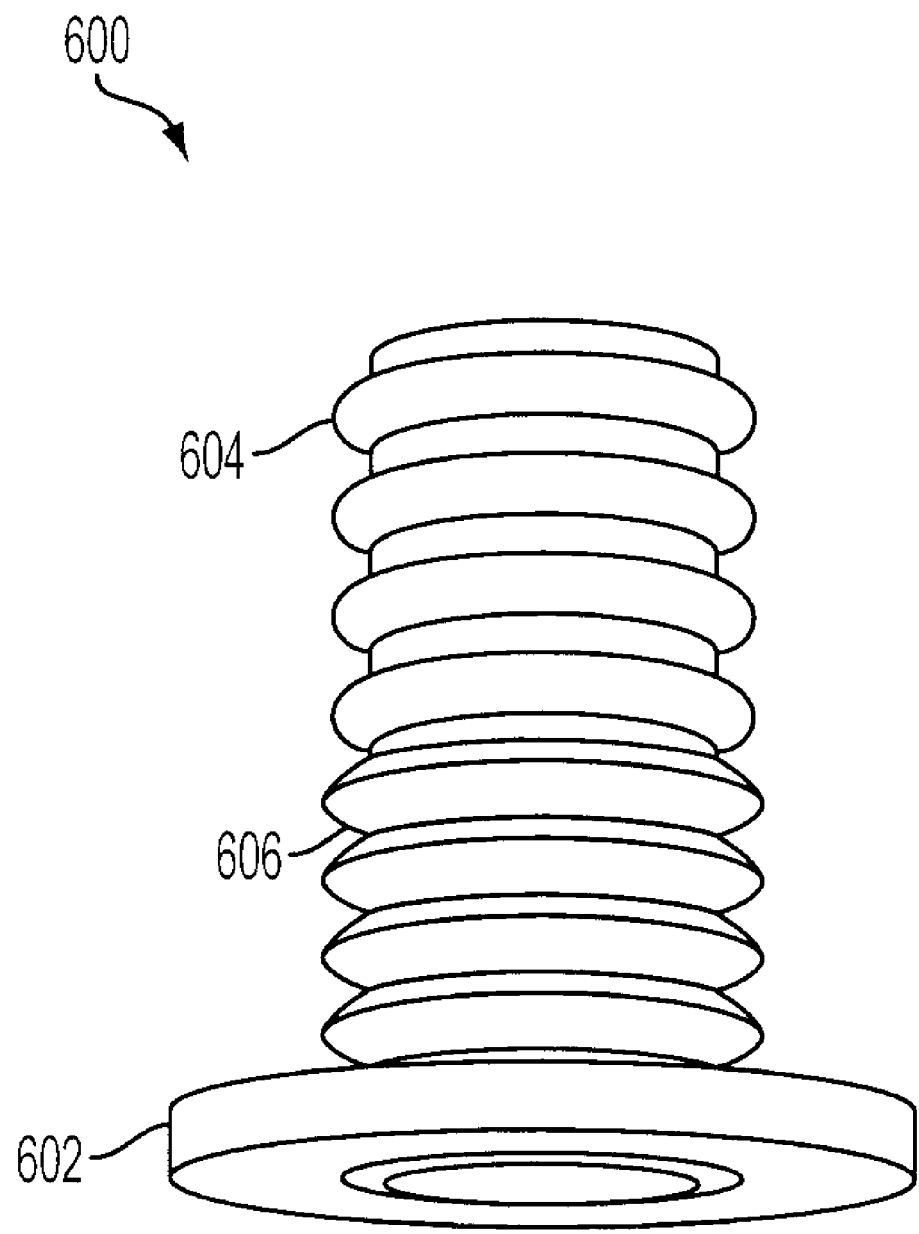
FIGS. 6A-B depict exemplary anastomosis connector clip.
Figure 6B:
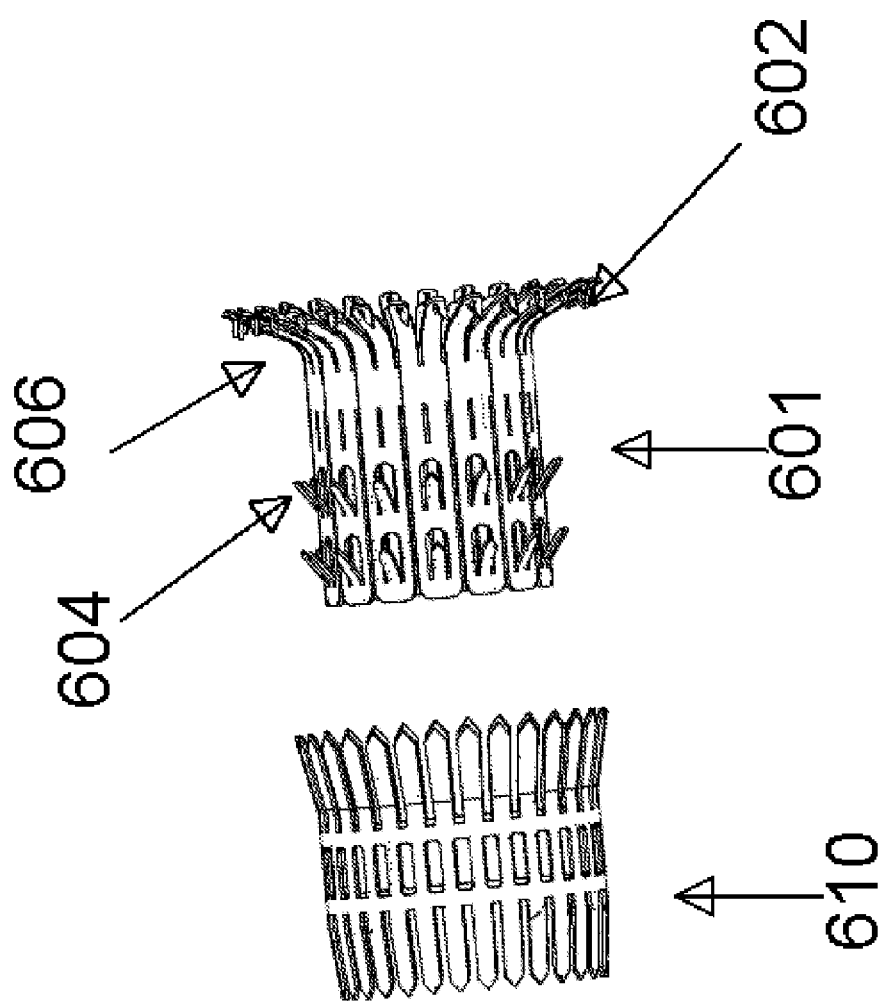

FIGS. 6A-6B depict optional embodiments of the anastomosis connector clip 600 according to the present invention. FIG. 6A depicts a anastomosis clip connector 600 optionally made of solid material while FIG. 6B provides a stent like mesh configuration of connector clip 601. Both anastomosis connector clips comprise at least two segments: a first segment 602 comprising a base; a second segment 604 and an optional third segment 606. Optionally, clip 600 is provided with a corresponding clip ring 610 preferably to secure clip 600 to a grafted vessel (not shown), as well as to anchor the connector clip 600 preventing it from being displaced from the graft site.

Optionally, the anastomosis connector clip 600 according to the present invention may optionally and preferably be made of a dilatable and/or otherwise self-expanding structure, that is optionally shaped according to the graft site or vasculature at the graft site angle or the like.

The anastomosis connector clip 600 according to the present invention is preferably expandable from a low-profile compressed condition to a larger profile expanded condition, wherein the resilient material urges the vessel supporting structure to expand radially, and to thereby apply radial force against the blood vessel's inner wall surface. For example, balloon angioplasty may be utilized to provide the final shape of the connector clip.

A preferred embodiment of the present invention comprises an anastomosis connector clip 600 that may optionally be composed of a shape memory alloy (SMA) including but not limited to nickel titanium alloy (NiTi), also known as nitinol, having a transition temperature around body temperature. They may also (additionally or alternatively) optionally comprise a shape memory polymer (SMP) that can be triggered in response to changes in heat, pH, electric or magnetic fields. For example, the anastomosis connector clip of the preferred embodiment of the present invention may optionally be introduced into a blood vessel in its collapsed formation having a small profile. Once in place and after it is released from the constraining catheter, the device preferably expands to the appropriate diameter and into its final or "memorized" shape.

Figure 7B:
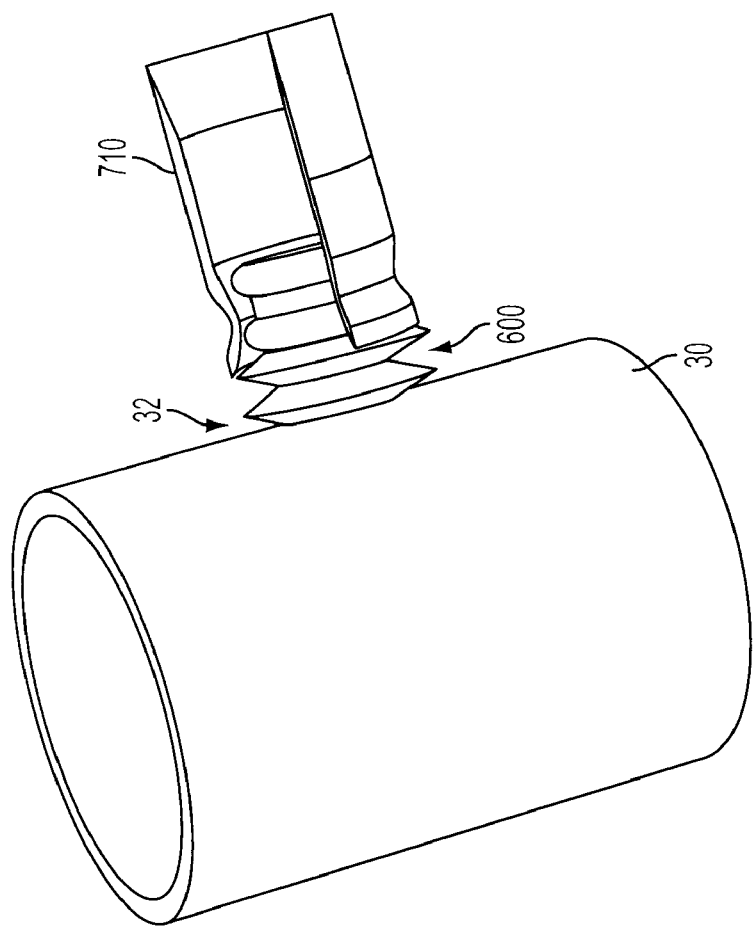
FIGS. 7A-B depicts an exemplary anastomosis connector clip within the graft site.
Figure 7A:
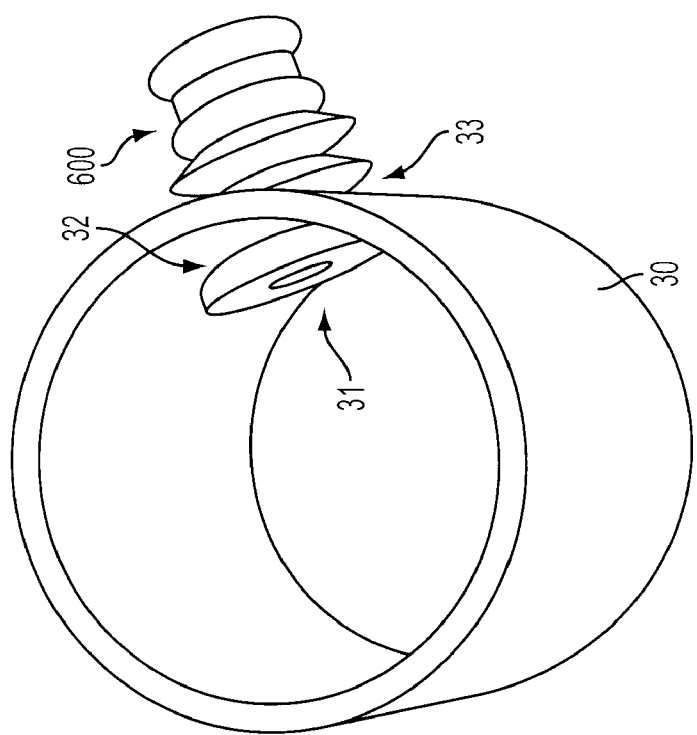

FIGS. 7A-7B depicts optional perspective views of an anastomotic vessel using the solid anastomosis connector clip 600 depicted in FIG. 6A. FIG. 7A depicts connector 600 extending from the aortic endoluminal graft site 31 to the external graft site 33. FIG. 7B depicts a perspective view of the external surface of aorta 30 at graft site 32 wherein vessel 710 is grafted along second segment 604 of the anastomotic connector clip 600 shown in FIG. 6.

FIGS. 8A-B show a number of views of an optional embodiment of the present invention wherein an external support member 802 is coupled to the anastomotic connector clip assemblies depicted in FIGS. 7A and 7B respectively. FIG. 8C further depicts an anastomosis clip fastening ring 804 fastening the connector clip assembly to grafted vessel 810 optionally by applying pressure.

Optionally, fastening device 804 may optionally and preferably form and determine the required graft angle. Optionally, the fastening device 804 may form up to about 90 degrees, most preferably about 30 degrees or about 45 degrees or about 60 degrees and optionally 90 degrees. Optionally the connector clip ring 804 fastens the connector clip and graft together by applying pressure, for example, fastening may optionally be achieved by methods including but not limited to applying pressure, stapling, releasing or inflating an angioplasty balloon or the like coupling tools. Optionally, fastening may be achieved by use of hooks along an external ring clip.

While the invention has been described with respect to a limited number of embodiments, it will be appreciated that many variations, modifications and other applications of the invention may be made.

What is claimed is:

1. A method for performing a minimally invasive endoluminal proximal CABG (Coronary Artery Bypass Graft) anastomosis on an aorta using an anastomosis connector clip, the method comprising:
   performing a thoracotomy on at least one side of the body to define a thoracic port;
   identifying an anastomosis graft site on an external surface of the aorta;
   defining a femoral artery port, such that an endoluminal side of said graft site is accessed through said femoral artery port and an external surface of said graft site is accessed through said thoracic port;
   disposing an isolating ring stabilizer over the aorta through said thoracic port;
   stabilizing said graft site with said isolating ring stabilizer disposed over the external surface of said graft site to provide a stabilized graft site;
   puncturing said stabilized graft site to provide a graft site port and a graft site channel through which a guidewire is threaded;
   advancing said guidewire through the vasculature to said femoral artery port, said advancing said guidewire comprising retrieving said guidewire at said femoral artery port and threading said anastomosis connector clip on said guidewire;
   deploying said anastomosis connector clip from the endoluminal side through to the external surface of said graft site channel by said guidewire;
   supporting said anastomosis connector clip in said graft site channel from the external surface of said graft site;
   coupling a connector clip external support member to said anastomosis connector clip over said graft site channel;
   disposing a graft vessel over said anastomosis connector clip on said graft site external surface; and
   coupling said graft vessel and said connector clip external support member to said connector clip.

2. The method of claim 1 further comprising deploying an anastomosis clip fastening device for securely fastening said graft vessel to said anastomosis connector clip.

3. The method of claim 1 wherein said graft site isolation and stabilization is achieved using vacuum.

4. The method of claim 3 wherein said vacuum is applied to a flexible pillow associated with said isolating ring stabilizer disposed over said graft site.

5. The method of claim 1 wherein said anastomosis connector clip is introduced from said femoral port over said guidewire using a clip introducer loaded with said anastomosis connector clip.

6. The method of claim 5 wherein said graft site channel is perforated with a tool originating from said femoral port over said guidewire.

7. The method of claim 6, wherein said tool is separate from said clip introducer.

8. The method of claim 6, wherein said tool is combined with said clip introducer.

9. The method of claim 8 wherein said tool is selected from the group consisting of a needle introducer and a tissue punch.

* * * * *